US011703423B2

(12) United States Patent
Cettour-Janet

(10) Patent No.: US 11,703,423 B2
(45) Date of Patent: Jul. 18, 2023

(54) METHOD FOR DRIVING A TIRE ON A WEAR ROLLING ROAD

(71) Applicant: COMPAGNIE GENERALE DES ETABLISSEMENTS MICHELIN, Clermont-Ferrand (FR)

(72) Inventor: Dominique Cettour-Janet, Clermont-Ferrand (FR)

(73) Assignee: COMPAGNIE GENERALE DES ETABLISSEMENTS MICHELIN, Clermont-Ferrand (FR)

(*) Notice: Subject to any disclaimer, the term of this patent is extended or adjusted under 35 U.S.C. 154(b) by 349 days.

(21) Appl. No.: 17/264,682

(22) PCT Filed: Jul. 30, 2019

(86) PCT No.: PCT/EP2019/070488
§ 371 (c)(1),
(2) Date: Jan. 29, 2021

(87) PCT Pub. No.: WO2020/025606
PCT Pub. Date: Feb. 6, 2020

(65) Prior Publication Data
US 2021/0302274 A1  Sep. 30, 2021

(30) Foreign Application Priority Data
Jul. 31, 2018 (FR) ..................... 1857142

(51) Int. Cl.
G01M 17/02      (2006.01)
G01N 3/56       (2006.01)
(Continued)

(52) U.S. Cl.
CPC ............ G01M 17/024 (2013.01); G01N 3/56 (2013.01); G01M 99/007 (2013.01); G01N 2033/0085 (2013.01)

(58) Field of Classification Search
CPC ............ G01M 17/065; G01M 17/022; G01M 99/007; B60C 99/006; B60C 11/246
See application file for complete search history.

(56) References Cited

U.S. PATENT DOCUMENTS

| 2005/0066719 | A1* | 3/2005 | Turner ................. G01M 17/02 73/146 |
| 2009/0012763 | A1 | 1/2009 | Langer et al. |
| 2018/0201077 | A1 | 7/2018 | Xie et al. |

OTHER PUBLICATIONS

International Search Report dated Nov. 6, 2019, in corresponding PCT/EP2019/070488 (4 pages).

* cited by examiner

Primary Examiner — Eric S. McCall
Assistant Examiner — Timothy P Graves
(74) Attorney, Agent, or Firm — Venable LLP

(57) ABSTRACT

A method for testing the wear of tires running on a rolling road comprises the following steps: using the construction data of the vehicle and a dynamic equilibrium model, determining the relationship between the speed and the accelerations at the centre of gravity of the vehicle, and the angles and directional forces applied on a given axle; continuously recording the speed and the accelerations of a vehicle travelling on a predetermined route; and disposing the two tires belonging to a same axle on the rolling road and, depending on the recorded speed and acceleration values, the values of the angle of camber, load and longitudinal forces are applied, at all times, on each of the wheels of the axle. The values of the transverse forces undergone by each of the wheels are measured and the drift angle is varied so that the sum of the transverse forces resulting from the drifting of the tires is equal, at all times, to the transverse force applied to the centre of the axle and so that the (Continued)

difference in drift between the two wheels respects the variation in alignment imposed on the axle.

13 Claims, 2 Drawing Sheets

(51) Int. Cl.
*G01M 99/00* (2011.01)
*G01N 33/00* (2006.01)

METHOD FOR DRIVING A TIRE ON A WEAR ROLLING ROAD

BACKGROUND

The invention pertains to the field of tyre wear tests, and in particular to wear tests carried out on rolling machines.

The vast majority of tyre wear tests are carried out on road circuits which have been duly catalogued and on which experimental vehicles follow standardized courses.

This manner of evaluation remains a significant consumer of resources, however. Thus, many years ago, test protocols were developed to carry out these tests on rolling machines.

However, the protocols developed by the various test laboratories struggle to reproduce actual rolling conditions and to propose reliable classifications of the tyres with respect to one another as regards their performance in terms of wear.

Moreover, these tests are largely dependent on the types of vehicles and the characteristics of their front and rear suspensions, on the loads supported, on the type of driving, on the running speeds, on the circuits travelled on, on the nature of the road surfaces encountered, on the atmospheric conditions that prevail during the test, etc.

To this end, the most effective evaluation protocols on a test machine use physical models that make it possible to describe the dynamic effects of the vehicle on the tyre.

These models describe the equations that link the speeds and accelerations applied at the centre of gravity of the vehicle to the torsors of the forces applied at the wheel centres Fx, Fy, Fz, Cx, Cy, Cz. The dynamic equilibrium of the vehicle thus depends on the steering control and the vehicle translational speed imposed by the driver, resulting in roll and pitch angles imposed by the mechanical construction of the suspensions of the vehicle, and leading to the drift and camber angles and to the loads supported by each of the wheels of the vehicle.

In order to describe the behaviour of the tyre, these equations use known physical models such as, for example, the model developed by Hans Bastiaan Pacejka (Tyre modelling for use in vehicle dynamics studies, 1987 January Society of Automotive Engineers, Warrendale, Pa.). These non-linear models are based on mathematical models adapted to an experimental characterization of the tyre under different loads and drift and camber angles, and under longitudinal sliding as are allowed on tyre measurement machines of the Rat-Track type sold for example by the company MTS or on rolling drums with a large enough diameter for the curvature of the ground to have a negligible effect on the forces and moments produced by the tyre compared with flat ground. It is also possible to implement more or less refined physical modelling of the tyre ranging from a macro-structural breakdown to a finite element description in order to obtain the set of characteristics describing the behaviour of said tyre.

Alternatively, these laws can be optimized with the aid of experimental acquisitions by instrumenting a vehicle while it is running, or more simply, by taking measurements on a dynamometric platform as described for example in the standard AMTI Model OR6-5-2000.

The publication EP 1 354 184 discloses an experimental model that is able to respond to this concern.

That publication proposes carrying out the following steps.

A first step consists in characterizing the vehicle by measuring, with the aid of a dynamometric platform, the directional forces Fx, Fy, Fz and the drift and camber angles encountered by each of the tyres during this step of characterizing the vehicle, during which the vehicle is driven on the platform with different accelerations, translational speeds and cornering radii.

The second step of the method according to EP 1 354 184 consists in characterizing a wear test course by measuring the accelerations and the speeds at the centre of gravity of the vehicle when the vehicle runs on the test course, which is preferably identical to the test course used to carry out the tests under actual running conditions and on which experimental wear results have already been acquired. This second step may be independent of the vehicle and of the set of tyres used.

During a third step of the method, the experimental results acquired during the first step make it possible to create experimental laws specific to the vehicle and to the set of tyres, and linking the three directional forces Fx, Fy and Fz, and the drift angle that are applied at the wheel centre and encountered by each of the tyres, to the accelerations (Ax, Ay) and to the translational speed (Vx) of the vehicle, which are measured at the centre of gravity.

By using a dynamic model of the vehicle, and after the geometry of the rolling sets has been described, associated with a model of the tyre such as the one developed by Hans Bastiaan Pacejka, it is possible, in an equivalent manner, to determine by calculation these relationships, dispensing with the first step.

Finally, the actual test step consists in mounting a wheel supporting the tyre to be tested on a rolling road, and in controlling the test machine to apply to the wheel the forces Fx, Fy, Fz and the drift angle that are encountered by the tyre during the test course and are calculated from laws obtained during the third step and from acceleration and drift data acquired during the second step. Thus, by travelling on the rolling road a distance similar to that covered by the vehicle on the reference wear circuit, the performance in terms of wear that is recorded on said circuit is reproduced on the tyre tested.

Although this method makes it possible to obtain satisfactory wear results that are similar to the results obtained on the test circuit by a vehicle, it has the drawback of employing, during the first step, experimental plans that are difficult and expensive. Similarly, the determination by experimental identification (i.e. Pacejka model) of the dynamic laws taking into account the operation of the tyre is difficult and complex and cannot be carried out in real time. The same goes if a pure tyre modelling approach is adopted in order to evaluate these same operating characteristics.

The object of the invention is to propose a tyre wear test method that makes it possible to simplify the above-described procedure and to lessen the costs and calculation times necessary to carry it out.

SUMMARY

The method for testing wear on tyres running on a rolling road of a test machine comprising at least one pair of measurement stations according to the invention provides for the implementation of steps in which:

Step A: with the aid of the construction data of a vehicle and of a dynamic equilibrium model, the relationships between the translational speed and the accelerations at the centre of gravity of the vehicle and the longitudinal forces, transverse forces and the variations in loads applied by each axle to a chassis of the vehicle, the distribution of the longitudinal forces and of the variations in loads applied by the ground to each of the wheels, and the camber angle of each of the wheels are determined, Step B: the translational speed and the accelerations at the centre of gravity of the vehicle when the vehicle is travelling on a predetermined wear test course are measured and recorded continuously, Step C: the two tyres belonging to one and the same axle are disposed on each of the measurement stations of the test machine, and, with the aid of the relationships determined in step A and depending on the values of translational speed and longitudinal acceleration, transverse acceleration and vertical acceleration recorded in step B, the values of the longitudinal force, of the transverse force and of the vertical force relative to said axle, and the values of camber angle, of load and of longitudinal forces relative to each of the wheels of said axle are determined at all times, the values of camber angle and the values of the longitudinal and vertical forces previously calculated are applied to each of the wheels at all times, and the values of the transverse forces to which each of the wheels of said axle are subjected are measured and the drift angle of each of the wheels is varied such that the sum of the transverse forces resulting from the skewing of the tyres is equal at all times to the transverse force applied to the centre of the axle and such that the difference in drift between the two wheels respects the variation in parallelism calculated on the basis of the characteristics of the axle.

It has been demonstrated that the laws used by the dynamic equilibrium models of vehicles make it possible to calculate the values of the roll and camber angles and the values of the longitudinal force, of the transverse force and of the vertical force applied to said axle, and that the values of load and acceleration relative to each of the wheels of said axle depending on the values of acceleration and translational speed at the centre of gravity can be easily accessible with the aid of the mechanical and geometric data of the vehicle. These laws can be formulated for example on the basis of a model known as the quadricycle model, which is known per se.

Unlike the models for evaluating the transverse forces that are applied to each of the tyres of one and the same axle, such as the abovementioned model developed by Hans Bastiaan Pacejka or its equivalents, which make it necessary to take complex measurements or to introduce non-linear laws taking into account the behaviour of the tyre when the latter is subjected to variations in drift, load, camber angle and longitudinal sliding, the method according to the invention proposes dispensing with these steps by considering that the transverse force applied to the axle is the resultant of the lateral forces to which each of the tyres is subjected forming a drift angle with the longitudinal direction.

The test machine is thus controlled to "seek" the drift angle to be conferred on the tyres such that the sum of the transverse forces measured on each of the wheels is equal to the transverse force applied to the axle while respecting the differences in steering angles of each of the wheels that are imposed by the geometry of the axle.

This is thus an operating principle referred to as "hardware in the loop". In other words, since the value of the drift angle and of the lateral forces is not known individually for each of the tyres of the axle, it is the controlling of the machine that determines the angular value of the drift such that the sum of the lateral forces to which each of the tyres is subjected is equal to the lateral force at the axle while ensuring the difference in parallelism between the wheels of said axle, these two terms being easily accessible by using the quadricycle model.

The wear test method thus makes it possible to dispense with the experimental characterization and the modelling for describing the tyre and also affords the possibility, once the construction data of the vehicle have been acquired, to test any sets of tyres for this vehicle.

The method according to the invention also makes it possible to take into account the change in the physical properties of each of the tyres depending on the progression of the degree of wear thereof during the test. Specifically, the test machine automatically adapts the drift angles of each of the tyres of the axle in question in order to obtain the desired value of the total transverse force applied to the axle. By contrast, in an approach involving experimental characterization or modelling of the characteristics of the tyre, it would ideally be necessary to change these characteristics during the test depending on the wear in order to continuously adapt the driving of the tyre to the test machine, this becoming very difficult in practice.

The wear results thus faithfully approach the results obtained when running the vehicle on the selected test course.

The wear tests can thus be obtained under very favourable economic conditions and in shorter times.

The test method according to the invention may also involve, alone or in combination, the execution of the following actions:

The value of the longitudinal force applied by each axle to the chassis results from the dynamic equilibrium model of the vehicle under the effect of the longitudinal acceleration, the construction data of the vehicle, the translational speed and the tensile forces supplied by the engine.

The longitudinal forces applied by the ground to each of the wheels of one and the same axle are equal at all times.

The distribution between the longitudinal forces applied by the ground to each of the four wheels results from a specific control law introduced into the dynamic equilibrium model of the vehicle.

The sum of the variations in loads applied by the ground to each of the wheels of one and the same axle results from the pitch dynamic equilibrium model of the vehicle under the effect of the speed, the longitudinal acceleration and the construction data of the vehicle.

The difference in the variations in loads applied by the ground to each of the wheels of one and the same axle results from the roll dynamic equilibrium model of the vehicle under the effect of the transverse acceleration and the construction data of the vehicle.

The value of the transverse force applied by each axle to the chassis results from the yaw dynamic equilibrium model of the vehicle under the effect of the transverse acceleration and the construction data of the vehicle.

The camber angle of each wheel results from the roll dynamic equilibrium model of the vehicle under the effect of the transverse acceleration and the construction data of the vehicle.

The value of the camber angle is corrected such that this angle results from the corrected dynamic equilibrium model of the effect of elastic variations in camber angle that are brought about by the transverse forces measured at all times on the rolling road.

The drift angles of each of the wheels of one and the same axle are varied such that the difference between the drift angles of each of the wheels is equal to a known value.

The value of the difference between the drift angles of each of the wheels of one and the same axle is zero at all times.

The value of the difference between the drift angles of each of the wheels of one and the same axle is corrected such that this difference results from the corrected dynamic equilibrium model of the effect of the value of the elastic variations in steering angle that are brought about by the variations in load and the longitudinal forces calculated, and by the transverse forces measured at all times on the rolling road.

The test machine is equipped with a plurality of pairs of measurement stations such that it is possible to carry out:

tests of sets of tyres mounted on the front and rear axles of one and the same vehicle, tests of different sets of tyres belonging to one and the same axle of one and the same vehicle, tests of sets of tyres mounted on the same axle of one and the same vehicle, involving different adjustments of the construction data of the vehicle, tests of identical (or different) sets of tyres mounted on the same axle of different vehicles, tests of different sets of tyres mounted on the same axle of different vehicles.

BRIEF DESCRIPTION OF THE DRAWINGS

The invention will be understood better from studying the appended figures, which are provided by way of example and are in no way limiting, and in which.

DETAILED DESCRIPTION

Figure 1:
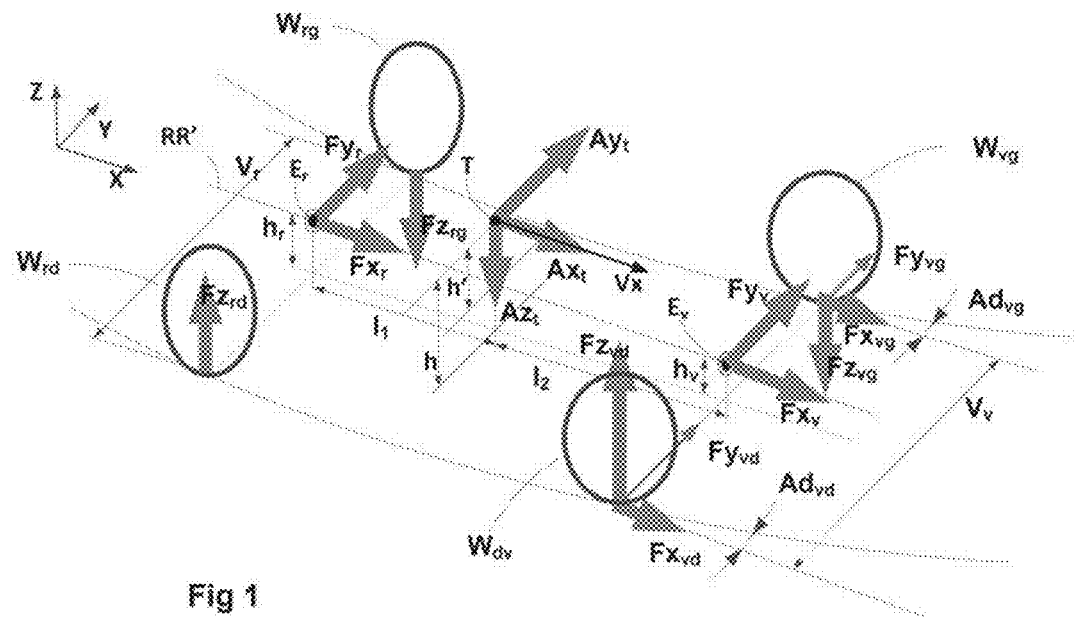
FIG. 1 shows a schematic view of a vehicle and resultants of the forces applied to each of the tyres.

With reference to FIG. 1, the vehicle is schematically shown by way of the left front wheel $W_{vg}$ on the inside of the bend, the right front wheel $W_{vd}$ on the outside of the bend, which are mounted on the front axle $E_v$, and by way of the left rear wheel $W_{rg}$ on the inside of the bend and by the right rear wheel $W_{rd}$ on the outside of the bend, which are mounted on the rear axle $E_r$. It goes without saying that the right and left wheels can be positioned either on the inside or on the outside of the bend depending on the aspect of the vehicle.

The same laws and the same phenomena apply to the front axle $E_v$ and to the rear axle $E_r$. Thus, for ease of understanding, reference will be made to the front of the vehicle by adding an index "v" to the forces or angles observed on the front axle $E_v$ and an index "r" to the forces or angles observed on the rear axle. The lack of an index then refers, without distinction, to the forces or angles observed on the front axle or on the rear axle. Similarly, where this will be useful for the understanding of the invention, the right-hand side and the left-hand side of the vehicle will be indicated by annotating the forces or the angles with an index "d" or "g", respectively. Finally, the values of the accelerations at the centre of gravity T are indicated with the aid of an index "t".

The vehicle is thus inscribed in its frame of reference in which the axis X represents the longitudinal axis, the axis Y represents the transverse axis, and the axis Z represents the vertical axis.

The centre of gravity T of the vehicle is disposed at a height h above the ground and at a height h' above the roll axis RR' passing through the front axle $E_v$ and through the rear axle $E_r$. The centre of gravity T is at a distance from the rear axle by a value $I_1$ and from the front axle by a value $I_2$, respectively. The centres of roll of the front axle $E_v$ and of the rear axle $E_r$ are disposed at a height $h_v$ and $h_r$, respectively, above the ground. Vv and Vr represent the width of the front and rear paths.

These geometric values, and the elastokinematic construction features of the vehicle, are introduced into the dynamic equilibrium model. Added to these mechanical data are the distribution value of the mass of the vehicle, the values of the toe-in angles (Ap) or of the static camber angles (Acs) conferred on each of the wheels, elements for describing the stiffness and the dynamics of the suspension elements and anti-roll bars, data relating to the aerodynamic coefficients of the vehicle and data relating to the resistance to forward travel of the tyres.

The entirety of the construction data of the vehicle is identified by the common denomination Dc.

Figure 3:
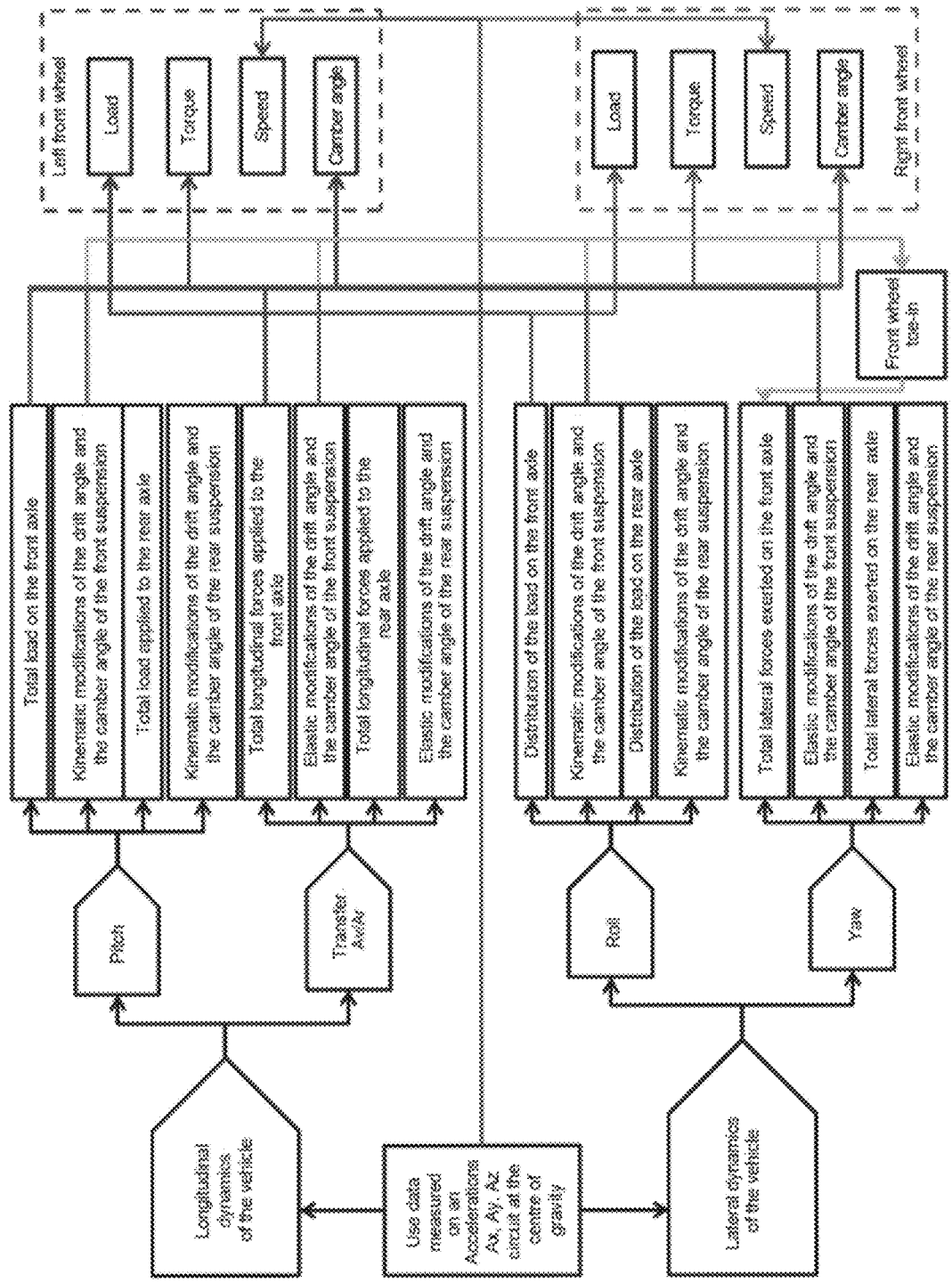
FIG. 3 is a diagram illustrating the interactions between the different forces taken into account in the dynamic equilibrium model of the vehicle.

With reference to FIG. 3, the kinematic and dynamic equilibrium model, referred to as the "quadricycle" model, of the vehicle, will thus make it possible to calculate the values of the forces exerted on the front axle and on the rear axle when the vehicle travels at a translational speed Vx and is subjected to longitudinal accelerations $Ax_t$, transverse accelerations $Ay_t$ and vertical accelerations $Az_t$ at the centre of gravity T.

With the aid of the equations describing the lateral and longitudinal dynamics of the vehicle resulting from the forces applied at the centre of gravity, the following are determined:

a distribution of the variations in loads applied to each of the front or rear axles $Fz_v$, $Fz_r$ and the dynamic modifications of the drift angle Ad and of the camber angle Ac of the front and rear sets depending on the pitch, a distribution of the longitudinal forces applied to each of the front or rear axles $Fx_v$, $Fx_r$ and the elastic modifications of the drift angle Ad and of the camber angle Ac of the front and rear sets depending on the transfers of load between the front and rear axles, a distribution of the variations in loads $Fz_{vg}$, $Fz_{vd}$, $Fz_{rg}$, $Fz_{rd}$ on each of the wheels $Wv_g$, $Wv_d$, $Wr_g$, $Wr_d$ of the front or rear axle and the dynamic modifications of the drift angle Ad and of the camber angle Ac depending on the roll, the total lateral forces $Fy_v$, $Fy_r$ exerted on the front or rear axle and the elastic modifications of the drift angle Ad and the camber angle Ac of the front and rear sets depending on the yaw dynamic equilibrium.

The values of load, (braking or engine) torque, translational speed and camber angle to be applied to each of the wheels are deduced therefrom.

During step A, the dynamic model of the vehicle is therefore used to calculate the values of the forces and angles applied to the axle.

The longitudinal force applied by the axle to the chassis, $Fx=f_1(Ax_t, Vx, Dc)$, is the resultant of the braking and acceleration forces $Ax_t$, and of the forces necessary for opposing the aerodynamic resistance of the air and the frictional forces.

The difference $Fx_g-Fx_d$ of the longitudinal forces applied by the ground to each wheel can be considered to be zero assuming that the differential disposed on each of the axles or that the brake system, apart from the functions of the ABS or ESP type, share these forces equally. Otherwise, the dynamic equilibrium model of the vehicle should include a specific control law describing the manner of distribution of the longitudinal forces ($Fx_{vg}$, $Fx_{vd}$, $Fx_{rg}$, $Fx_{rd}$) between the four wheels of said vehicle, in the same way as is done on four-wheel drive vehicles, or in the front/rear distribution of the braking forces or motive forces.

The sum of the variations in loads applied by the ground to each of the wheels of one and the same axle is the resultant of the distribution of the variations of loads in the vehicle and of the pitch equilibrium equation of the vehicle under the effect of the speed Vx and the longitudinal acceleration $Ax_t$: $Fz_g+Fz_d=f_2(Ax_t, Vx, Dc)$ The difference of the variation in load applied by the ground to each of the wheels of this same axle results from the construction data Dc of the vehicle and from the roll equilibrium equation under the effect of the transverse acceleration $Ay_t$: $Fz_g-Fz_d=f_3(Ay_t, Dc)$.

The transverse force Fy applied by each axle to the chassis is the resultant of the construction data Dc of the vehicle and the transverse acceleration linked to centripetal forces: $Fy=f_4(Ay_t, Dc)$.

The camber angle also results from the roll equilibrium equation under the effect of the transverse acceleration $Ay_t$ plus the static camber angle values Acs that are part of the construction data Dc of the vehicle: $Ac=f_5(Ay_t, Dc)$.

It will be seen here that the real-time measurement of the transverse forces $Fy_g$ and $Fy_d$ that are applied by the ground to the left wheel or the right wheel of one and the same axle and are observed on the measurement rolling road 11 during step C makes it possible to refine the manner in which the value of the camber angles is obtained.

Specifically, under the effect of the transverse forces $Fy_g$ and $Fy_d$, the camber angles applied to each of the wheels need to be corrected in order to take account of the elastic deformations applied to the axle.

In order to refine the calculation, it is possible to introduce, from the values $Fy_g$ and $Fy_d$ measured on the rolling road 11, a secondary interactive loop such that the law for determining the camber angle becomes, for example $Ac_{vd}=f_5(Ay_t, Fy_{vd}, Fy_{vg}, Dc)$ for the right front wheel and $Ac_{vg}=f_5(Ay_t, Fy_{vd}, Fy_{vg}, Dc)$ for the left front wheel.

The difference between the drift angles applied to the right wheel $W_d$ and to the left wheel $W_g$ is generally derived from the construction data of the vehicle, and can be obtained with the aid of a law $\delta(Ad)$ which depends on the static toe-in or opening adjustments and the steering angle rules imposed mechanically on each of the front or rear paths, corrected by the dynamic variations linked to the pitch and roll movements applied to the wheels: $\delta(Ad)=f_6(Dc)$.

For the same reasons as those that were explained above, it may prove useful to take into account the elastic deformations of the front set (or of the rear set) that are brought about by the longitudinal forces $Fx_{vg}$, $Fx_{vd}$ applied by the ground to the left and right front wheels and the variations in vertical load $Fz_{vg}$, $Fz_{vd}$ applied by the ground to the left and right front wheels, and calculated with the aid of the dynamic equilibrium model, and by the transverse forces $Fy_{vg}$, $Fy_{vd}$ applied by the ground to the left and right front wheels that are measured on the rolling road in real time during step C. The difference between the drift angles $\delta(Ad)$ then becomes (for example for the front wheels) of the type $\delta(Ad)=f_6(Dc, Fx_{vg}, Fx_{vd}, Fy_{vg}, Fy_{vd}, Fz_{vg}, Fz_{vd})$.

It will be seen that these laws, which are specific to a vehicle, are not dependent on the nature of the tyre and can be implemented without it being necessary to have an operating model of the tyre.

Step B of the method consists in collecting translational speed and acceleration data that are representative of running under real conditions on a circuit that is representative of the wear conditions encountered by a tyre while it is being used on a correctly adjusted vehicle driven by a driver applying the level of driving harshness targeted by the "standard" of the test.

This course therefore comprises winding running portions, urban sections and motorway sections having standard road surfaces. Similarly, the running conditions are on dry ground, it being ensured that braking and acceleration operations are carried out in a manner corresponding to the "standard" driving harshness level, while respecting the set speed limits.

A recorder, disposed at the centre of gravity T of the vehicle, continuously records, in real time, the speed data Vx and acceleration data $Ax_t$, $Ay_t$, $Az_t$ to which the vehicle is subjected throughout the test course.

These recorded data are specific to the test course, to the "standard" harshness level, and are independent of the type of vehicle used for the recording.

Figure 2:
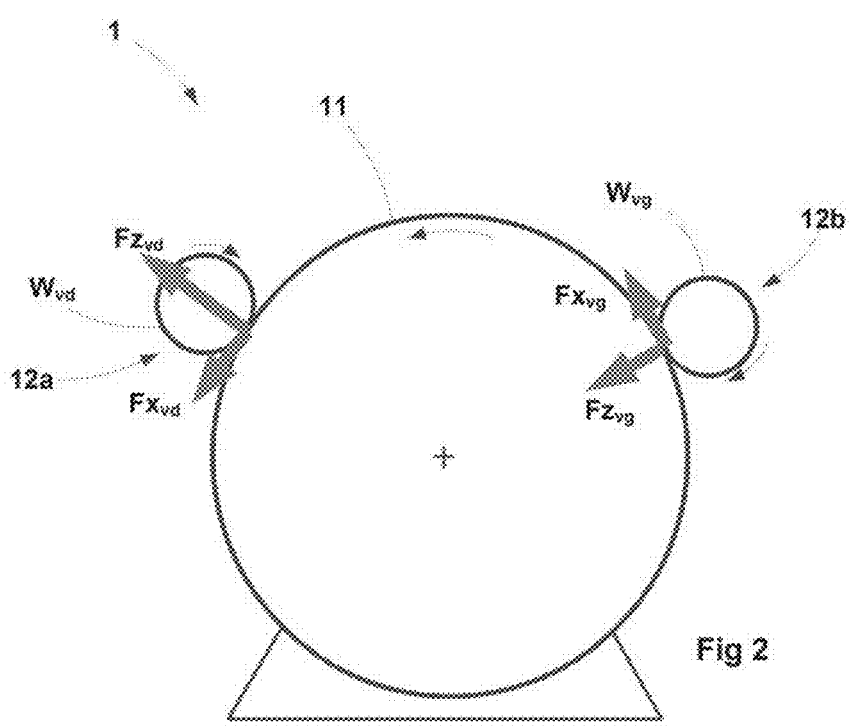
FIG. 2 is a schematic view of a rolling machine.

Step C of the implementation of the method according to the invention is the actual test step. The rolling test machine (1) as illustrated in FIG. 2 comprises a rolling road 11 driven in rotation by a motor (not shown). The machine has at least two measurement stations (12a, 12b) that are each mounted on an instrumented arm (not shown) supporting two hubs that are each intended to receive a wheel on which a tyre is mounted and which represent the right wheel $W_d$ and the left wheel $W_g$ of one and the same axle.

It is quite possible, in an equivalent manner, to carry out the tests according to the invention on a test machine of the flat-track type of the type mentioned above.

It will be noted here that, given the above, the rolling road 11 of the test machine 1 can be equipped with a plurality of pairs of measurement stations (12a, 12b). This arrangement thus affords a large number of different test possibilities.

For example, tests could be carried out on sets of tyres mounted on the front and rear axles of one and the same vehicle, or different sets of tyres belonging to one and the same axle could be tested.

It is also possible to carry out tests on sets of tyres mounted on the same axle of one and the same vehicle having different adjustments of the elastokinematic construction data Dc, or to test identical or different sets of tyres mounted on the same axle of different vehicles.

The circumferential surface of the rolling road 11 has a coating specifically researched to faithfully reproduce the grading of road surfaces commonly encountered on the wear test circuit. These coatings can be changed during the test in order to more faithfully approach reality.

Each measurement station (12a, 12b) is equipped with means for varying the vertical deflection of the tyre, likened here to the load Fz borne by the tyre, the torques applied to the wheel and simulating the phases of acceleration or braking, the drift angle ($Ad_e$, $Ad_d$) and the camber angle ($Ac_d$, $Ac_e$) of each of the wheels, and means for continuously measuring the value of the forces ($Fx_d$, $Fy_d$, $Fz_d$) or ($Fx_g$, $Fy_g$, $Fz_g$) applied by the ground to each of the wheels. The rotational speed of the rolling road 11 is controlled so as to represent the speed Vx of forward movement of the vehicle.

With the aid of the laws $f_1$, $f_2$, $f_3$, $f_4$, $f_5$, $f_6$ determined in step A, and depending on the values of speed Vx and longitudinal, transverse and vertical acceleration $Ax_t$, $Ay_t$, $Az_t$ recorded in step B, the values of camber angle Ac, the values of the longitudinal force Fx, of the transverse force Fy and of the vertical force Fz relative to said axle E, and the values of load $Fz_g$, $Fz_d$ and of longitudinal forces $Fx_g$, $Fx_d$ relative to each of the wheels $W_g$, $W_d$ of the axle in question are determined at all times.

The values of camber angle Ac and the values of longitudinal and vertical force $Fx_g$, $Fx_d$, and $Fz_g$, $Fz_d$ to which each of the wheels is subjected when the vehicle travels along the wear test route are applied continuously and at all times to each of the wheels. Thus, the running conditions observed on the test circuit are reproduced in real time on a rolling machine.

Only the drift angle applied to each of the wheels remains to be determined.

To this end, the values of the transverse forces $Fy_g$, $Fy_d$ to which each of the wheels $W_g$, $W_d$ is subjected are measured and the drift angle $Ad_a$, $Ad_d$ of each of the wheels is varied such that the sum of the transverse forces $Fy_g + Fy_d$ resulting from the skewing of the tyres is equal at all times to the transverse force Fy applied to the centre of the axle E in question.

At the same time, the difference between the drift angles of the right wheel and of the left wheel $(Ad_d - Ad_a = \delta(Ad))$ is controlled so as to take account of the variation in parallelism brought about by the roll and pitch dynamics of the chassis.

As was seen above, this difference in steering angle is linked to the construction of the front or rear set. In the simplest cases, this difference can be zero at all times or incorporate the kinematics of the set in question or, more generally, take account of the elastic deformations caused by the longitudinal, vertical and transverse forces applied by the ground to the wheels.

Thus, the controlling of the test machine "steers" the drift angle of each of the wheels until the value of the sum of the transverse forces $Fy_g + Fy_d$ measured on each of the stations 12a and 12b of the machine supporting the right wheel $W_d$ and the left wheel $W_g$, respectively, is equal to the force Fy at this time.

The transverse forces $Fy_d$ and $Fy_g$ caused by each of the tyres on the rolling road 11 under the effect of the drift and camber angles under the load conditions $Fz_d$ and $Fz_g$, which naturally obey the non-linear laws forming the dynamic model of the tyre, are then reproduced with values representative of the actual running conditions.

The method that is the subject of the above description makes it possible to dispense with the complex calculations linked with determining the transverse forces, and to reliably and precisely reproduce, on a test machine, the running conditions in order to carry out a wear test on the tyres of a vehicle.

Terminology

1 Test machine for wear test.
11 Rolling road.
12a, 12b Measurement stations for the two tyres of one and the same axle.
$W_{vg}$ Left front wheel (inside of the bend).
$W_{vd}$ Right front wheel (outside of the bend).
$W_g$ Left rear wheel (inside of the bend).
$W_{rd}$ Right rear wheel (outside of the bend).
T Centre of gravity of the vehicle.
h Height of the centre of gravity with respect to the ground.
h' Height of the centre of gravity with respect to the roll axis of the vehicle.
$I_1$ Distance between the centre of gravity and the rear axle.
$I_2$ Distance between the centre of gravity and the front axle.
$Ax_t$ Longitudinal acceleration at the centre of gravity of the vehicle.
$Ay_t$ Transverse acceleration at the centre of gravity of the vehicle.
$Az_t$ Vertical acceleration at the centre of gravity of the vehicle.
Vx Translational speed.
$E_v$ Front axle.
$h_v$ Height of the centre of roll of the front axle with respect to the ground.
$V_v$ Width of the front path.
$Fx_v$ Longitudinal force applied by the front axle to the chassis.
$Fx_{vg}$ Longitudinal force applied by the ground to the left front wheel.
$Fx_{vd}$ Longitudinal force applied by the ground to the right front wheel.
$Fy_v$ Transverse force applied by the front axle to the chassis.
$Fy_{vg}$ Transverse force applied by the ground to the left front wheel.
$Fy_{vd}$ Transverse force applied by the ground to the right front wheel.
$Fz_{vg}$ Variation in vertical load applied by the ground to the left front wheel.
$Fz_{vd}$ Variation in vertical load applied by the ground to the right front wheel.
$Ad_{vg}$ Drift angle of the left front wheel.
$Ad_{vd}$ Drift angle of the right front wheel.
$E_r$ Rear axle.
$h_r$ Height of the centre of roll of the rear axle with respect to the ground.
$V_r$ Width of the rear path.
$Fx_r$ Longitudinal force applied by the rear axle to the chassis.
$Fy_r$ Transverse force applied by the rear axle to the chassis.
$Fz_{rg}$ Variation in vertical load applied by the ground to the left rear wheel.
$Fz_{rd}$ Variation in vertical load applied by the ground to the right rear wheel.
RR' Roll axis.
Dc Elastokinematic construction data of the vehicle.

The invention claimed is:

1. A method for testing wear on tires running on a rolling road of a test machine comprising at least one pair of measurement stations, during which the following steps are carried out:
   (a) using construction data of a vehicle and a dynamic equilibrium model, determining relationships between the translational speed Vx and the accelerations $Ax_t$, $Ay_t$, $Az_t$ at the center of gravity of the vehicle, and (1) longitudinal forces Fx, (2) transverse forces Fy and (3) variations in loads Fz applied by each axle to a chassis of the vehicle, the distribution (4) of the longitudinal forces $Fx_{vg}$, $Fx_{vd}$, $Fx_{rg}$, $Fx_{rd}$ and (5) of the variations in loads $Fz_{vg}$, $Fz_{vd}$, $Fz_{rg}$, $Fz_{rd}$ applied by the ground to each of the wheels, and (6) the camber angle $A_c$ of each of the wheels;
   (b) continuously measuring and recording the translational speed Vx and the accelerations $Ax_t$, $Ay_t$, $Az_t$ at the center of gravity of the vehicle when the vehicle is travelling on a predetermined wear test course; and
   (c) disposing the two wheels belonging to a same axle on each of the measurement stations of the test machine, wherein, using the relationships determined in step (a) and depending on values of the translational speed Vx and longitudinal acceleration $Ax_t$, transverse acceleration $Ay_t$ and vertical acceleration $Az_t$ recorded in step (b), the values of the longitudinal force Fx, of the transverse force Fy and of the variation in load Fz applied by the axle to the chassis of the vehicle, and the values of camber angle $A_c$, of variations in loads $Fz_g$, $Fz_d$ and of longitudinal forces $Fx_g$, $Fx_d$ applied by the ground to each of the wheels of the axle are determined at all times, wherein the values of camber angle $A_c$ and the values of the longitudinal forces and variations in loads previously calculated are applied to each of the wheels at all times, and wherein values of the transverse forces $Fy_g$, $Fy_d$ to which each of the wheels of the axle are subjected are measured and the drift angle $A_d$ of each of the wheels is varied such that a sum of the transverse forces $Fy_g+Fy_d$ resulting from skewing of the tires is equal at all times to the transverse force Fy applied to the center of the axle and such that a difference in drift $\delta(A_d)$ between the two wheels respects a variation in parallelism calculated on a basis of the characteristics of the axle.

2. The method according to claim 1, wherein the value of the longitudinal force applied by each axle to the chassis results from the dynamic equilibrium model of the vehicle under the effect of the longitudinal acceleration $Ax_t$, the construction data $D_c$ of the vehicle, the translational speed Vx and the tensile forces supplied by the engine $Fx=f_1(Ax_t, Vx, Dc)$.

3. The method according to claim 2, wherein the longitudinal forces applied by the ground to each of the wheels of the same axle are equal at all times.

4. The method according to claim 2, wherein a distribution between the longitudinal forces applied by the ground to each of the four wheels results from a specific control law introduced into the dynamic equilibrium model of the vehicle.

5. The method according to claim 1, wherein a sum of the variations in loads $Fz_g+Fz_d$ applied by the ground to each of the wheels of the same axle results from a pitch dynamic equilibrium model of the vehicle under the effect of the speed Vx, the longitudinal acceleration $Ax_t$) and the construction data $D_c$ of the vehicle, $Fz_g+Fz_d=f_2(Ax_t, Vx, Dc)$.

6. The method according to claim 1, wherein a difference in the variations in loads applied by the ground to each of the wheels of the same axle results from a roll dynamic equilibrium model of the vehicle under the effect of the transverse acceleration $Ay_t$ and the construction data $D_c$ of the vehicle, $Fz_g-Fz_d=f_3(Ay_t, Dc)$.

7. The method according to claim 1, wherein the value of the transverse force Fy applied by each axle to the chassis results from a yaw dynamic equilibrium model of the vehicle under the effect of the transverse acceleration $Ay_t$ and the construction data $D_c$ of the vehicle, $Fy=f_4(Ay_t, Dc)$.

8. The method according to claim 1, wherein the camber angle $A_c$ of each wheel results from a roll dynamic equilibrium model of the vehicle under the effect of the transverse acceleration $Ay_t$ and the construction data $D_c$ of the vehicle, $Ac=f_5(Ay_t, Dc)$.

9. The method according to claim 8, wherein the value of the camber angle $A_c$ is corrected such that the camber angle $A_c$ results from a corrected dynamic equilibrium model of the effect of elastic variations in camber angle that are brought about by the transverse forces measured at all times on the rolling road, $Ac_{vd}=f'_5(Ay_t, Fy_{vd}, Fy_{vg}, Dc)$ and $Ac_{vg}=f'_5(Ay_t, Fy_{vg}, Fy_{vd}, Dc)$.

10. The method according to claim 1, wherein the drift angles of each of the wheels of the same axle are varied such that the difference $Ad_g-Ad_d$ between the drift angles of each of the wheels is equal to a known value $\delta(Ad)$, $\delta(Ad)=f_6(Dc)$.

11. The method according to claim 10, wherein the value of the difference between the drift angles of each of the wheels of the same axle $\delta(Ad)$ is zero at all times.

12. The method according to claim 10, wherein the value of the difference between the drift angles of each of the wheels of the same axle $\delta(Ad)$ is corrected such that the difference $Ad_g-Ad_d$ results from a corrected dynamic equilibrium model of the effect of the value of the elastic variations in steering angle that are brought about by the variations in load $Fz_{vg}$, $Fz_{vd}$ and the longitudinal forces $Fx_{vg}$, $Fx_{vd}$ calculated, and by the transverse forces $Fy_g$ and $Fy_d$ measured at all times on the rolling road, $\delta(Ad)=f'_6(Dc, Fx_{vg}, Fx_{vd}, Fy_{vg}, Fy_{vd}, Fz_{vg}, Fz_{vd})$.

13. The method according to claim 1, wherein the test machine is equipped with a plurality of pairs of measurement stations and wherein the following are carried out:
tests of sets of tires mounted on the front and rear axles of the same vehicle;
tests of different sets of tires belonging to the one axle of the same vehicle;
tests of sets of tires mounted on one axle of the same vehicle, involving different adjustments of the construction data of the vehicle $D_c$;
tests of identical sets of tires mounted on the same axle of different vehicles; and
tests of different sets of tires mounted on the same axle of different vehicles.

* * * * *